United States Patent [19]

Hunt et al.

[11] Patent Number: 4,495,817

[45] Date of Patent: Jan. 29, 1985

[54] ULTRASONIC IMAGING DEVICE

[75] Inventors: John W. Hunt; Michael S. Patterson, both of Toronto, Canada

[73] Assignee: The Ontario Cancer Institute, Toronto, Canada

[21] Appl. No.: 498,007

[22] Filed: May 25, 1983

[30] Foreign Application Priority Data

May 26, 1982 [GB] United Kingdom ............. 8215357

[51] Int. Cl.$^3$ ............................................. G01N 29/04
[52] U.S. Cl. ........................................ 73/624; 73/642; 310/335
[58] Field of Search ............... 73/624, 642, 628, 641; 128/660; 310/335; 367/150

[56] References Cited

U.S. PATENT DOCUMENTS

| | | | |
|---|---|---|---|
| 3,965,455 | 6/1976 | Hurwitz ............................. | 310/335 |
| 4,025,805 | 5/1977 | Coltman et al. ..................... | 310/335 |
| 4,325,258 | 7/1982 | Foster ............................... | 73/642 |
| 4,339,952 | 7/1982 | Foster ............................... | 73/624 |

OTHER PUBLICATIONS

"Ultrasound Axicon: A Device for Focusing Over a Large Depth" C. B. Burckhardt, H. Hoffman and P. A. Grandchamp, *Journal of the Acoustical Society of America*, vol. 54, No. 6, pp. 1628 to 1630.
"Cylindrical Transducer Scatter Scanner" F. Stuart Foster et al., *Journal of the Acoustical Society of America*, vol. 68, pp. 85 to 92.
"The Conical Scanner: A Two Transducer Ultrasound Scatter Imaging Technique" F. Stuart Foster et al., *Ultrasound Imaging*, vol. 3, pp. 62 to 82.
"Acoustic Fields of Conical Radiators" M. S. Patterson et al., *I.E.E.E. Transactions on Sonics and Ultrasonics*, vol. SU29, Mar. 1982, pp. 83 to 92.

*Primary Examiner*—Anthony V. Ciarlante
*Attorney, Agent, or Firm*—Ridout & Maybee

[57] ABSTRACT

An ultrasonic imaging device includes a transducer assembly for transmitting ultrasound pulses into a portion of a structure to be imaged and receiving ultrasound scattered by said structure portion and generating signals in response thereto, means to energize said transducer assembly to transmit said pulses, scanning means for progressively relating said transducer assembly to successive portions of said structure according to a scanning pattern, and receiver and signal processing means for assembling an image from said generated signals, the transducer assembly comprising separate transmitting and receiving transducers, one of said transducers being a simulated conical transducer having a line focus, and the other of said transducers having its axis in parallel alignment with said line focus, the scanning means being operative to move said line focus in relation to a structure to be imaged in accordance with said scanning pattern. The simulated conical transducer includes a transducer element and an associated acoustic reflector system such that an active surface of the transducer element is perceived at said line focus as a conical transducer having a surface of much larger area than said active surface and having a half angle such that rays converge on said line focus at a predetermined angle of at least 20° to the latter. The transducer element may have a cylindrical active surface associated with a single conical reflector, a planar active surface associated with two conical reflectors.

12 Claims, 3 Drawing Figures

ULTRASONIC IMAGING DEVICE

This invention relates to ultrasound transducer assemblies and imaging devices utilizing such transducers.

Ultrasound imaging has several advantages over conventional x-ray imaging for medical applications. A thin cross-section of the internal structures of the body can be detected and mapped, with no harmful effects. Numerous ultrasound systems are available to display the structures of the body. The system used most widely has a single ultrasound transducer, or an array of transducers, which beams into the subject a short burst of ultrasound waves at a frequency in the range 1 to 10 MHz. When the beam encounters structures of the body, small reflected waves (generally called echoes) and directed back to the transducer. The transducer detects these echoes, and electronic circuits display the amplitude of signal vs time. The time between the echoes is related to the depth of the structures within the body, and is generally called the "range". The transducer is either placed in direct contact with the body through an acoustic coupling, or is placed in a water bath, at a considerable distance from the body. A mechanical system is used to scan the transducer across the body, and electronic systems translate this motion into a suitable Z-modulated X-Y display on a device such as an X-Y storage oscilloscope or analogue or digital scan converter. For example, for a linear translation of the transducer through a water bath, the X-direction is related to the position of the transducer, the Y-direction is related to the delay of the echoes, and the light intensity (Z-modulation) of the display system is related to the amplitude of the echoes. Therefore, a thin section of the body, called a tomographic image, is displayed.

Ultrasound imaging can also offer advantages in non-medical applications, such as the detection of flaws in opaque materials in applications where x-rays cannot be conveniently or safely utilized.

A major problem in conventional echographical ultrasound systems is the poor lateral spatial resolution. This is due to the lateral width of the transmitted and received ultrasound beams. Considerable improvement of the lateral resolution may be obtained by using a focused, large aperture transducer; however, this good resolution is at the expense of a very shallow depth-of-field. This may be overcome by using sophisticated electronic approaches to maintain focus through the image field. Even though some improvements have been obtained, resolution has been inadequate for detecting many types of small structure in the body. A further problem has been the formation of spurious images or artifacts due to reflection of ultrasound in unwanted modes.

Recently, Dr. F. Stuart Foster, of the Ultrasound Group, The Ontario Cancer Institute, developed ultrasound imaging systems which have overcome the depth-of-field limitations and, at the same time, have greatly improved the lateral resolution of the images. These systems are sometimes called "hybrid scanners". These are based on the use of cylindrical or conical transducer elements to generate converging wavefronts which produce a sharp line focus inside the body. A second transducer element is aimed along the line focus. The scattered waves received by this second transducer element allow the location of echogenic objects along the line focus to be determined. The functions of the transducers may if desired be reversed. The pair of transducers are fixed relative to each other, and move together as they scan across the object. The linear displacement of the transducer is monitored, and a tomographic image is formed in the manner previously described. Using this approach, high quality images can be obtained with excellent lateral resolution over all depths of the field, as is described more fully in articles by F. Stuart Foster, M. Arditi and J. W. Hunt "Cylindrical Transducer Scatter Scanner" J. Acoust. Soc. of Am.; Volume 68: pages 85–92 (1980), F. Stuart Foster, M. S. Patterson, M. Arditi and J. W. Hunt "The Conical Scanner: A Two Transducer Ultrasound Scatter Imaging Technique" Ultrasound Imaging, Volume 3: pages 62–82 (1981), and M. S. Patterson and F. Stuart Foster, "Acoustic Fields of Conical Radiators", IEEE Transactions on Sonics and Ultrasonics, Vol. SU29, March 1982: pages 83–92. Such systems are described in U.S. Pat. Nos. 4,339,952 and 4,325,258 issued to F. Stuart Foster on July 20, 1982 and Apr. 20, 1982, respectively.

In spite of the improvements in resolution which can be achieved with the above systems, there are some limitations in their existing practical embodiments as follows:

(a) The preferred conical transducer consists of a piezoelectric plastic film bonded to the inner face of an aluminum or steel cone (for a conical transducer). At the present time, the electro-mechanical efficiency of such piezoelectric plastics is rather poor, so that a high-voltage source is needed to generate ultrasound waves of the desired intensity.

(b) The low sensitivity of the plastic film means also that it is not well suited for detecting low amplitude scattered waves. Hence the large aperture of the cone cannot be adequately exploited in the receiving mode. Generally, it has proved desirable to use a high sensitivity transducer aligned with the axis of the cone as a receiver.

(c) The transmitted ultrasound radiation profile generated by the cone transducer has broad sidelobes around the line focus; these sidelobes can cause artifacts in the tomographic images: for example, the signal from a strong scatterer could mask that from a nearby weak scatterer.

In an endeavour to overcome these problems, we have developed an ultrasound imaging device and a transducer assembly for such a device which can provide the advantages of a conical transducer system utilizing piezoelectric film such as is discussed above and described in U.S. Pat. No. 4,325,258, but which is capable of much higher electro-mechanical acoustic efficiency, and can employ more conventional ultrasonic transducer elements.

According to the invention, a focusing ultrasonic transducer comprises a transducer assembly for transmitting and receiving ultrasound in an ultrasound imaging system, comprising separate transmitting and receiving transducers, one transducer having a line focus on the axis of a simulated conical active surface and the other transducer being aimed along that axis, characterized in that the simulated conical active surface is a virtual image, formed by an acoustic reflector system, of the active surface of a much smaller transducer element, such that rays from the reflector system converge on the line focus at an angle of at least 20° to the axis.

More specifically, the invention provides an ultrasonic imaging device, comprising a transducer assembly for transmitting ultrasound pulses into a portion of a structure to be imaged and receiving ultrasound scattered by said structure portion and generating signals in response thereto, means to energize said transducer assembly to transmit said pulses, scanning means for progressively relating said transducer assembly to successive portions of said structure according to a scanning pattern, and receiver and signal processing means for assembling an image from said generated signals, the transducer assembly comprising separate transmitting and receiving transducers, one of said transducers being a simulated conical transducer having a line focus, and the other of said transducers having its axis in parallel alignment with said line focus, the scanning means being operative to move said line focus in relation to a structure to be imaged in accordance with said scanning pattern, wherein the simulated conical transducer comprises a transducer element and an associated acoustic reflector system such that an active surface of the transducer element is perceived at said line focus as a conical transducer having a surface of much larger area than said active surface and having a half angle such that rays converge on said line focus at a predetermined angle of at least 20° to the latter.

The active surface of the transducer element may typically be a plane annulus or the outer surface of a cylinder. In the former case the reflector system requires two reflecting surfaces, a first convex frustoconical surface facing the free surface of the element and a second concave frusto-conical surface surrounding the first surface and facing away from the free surface of the element.

The transducer element may act as either transmitter or receiver, the other of these functions being performed by the transducer coaxial with and aimed along the focus line.

Further features of the invention will become apparent from the following description of preferred embodiments thereof with reference to the accompanying drawings in which.

In reach of the figures, the same reference numerals are used to indicate similar or analogous features.

Figure 1:
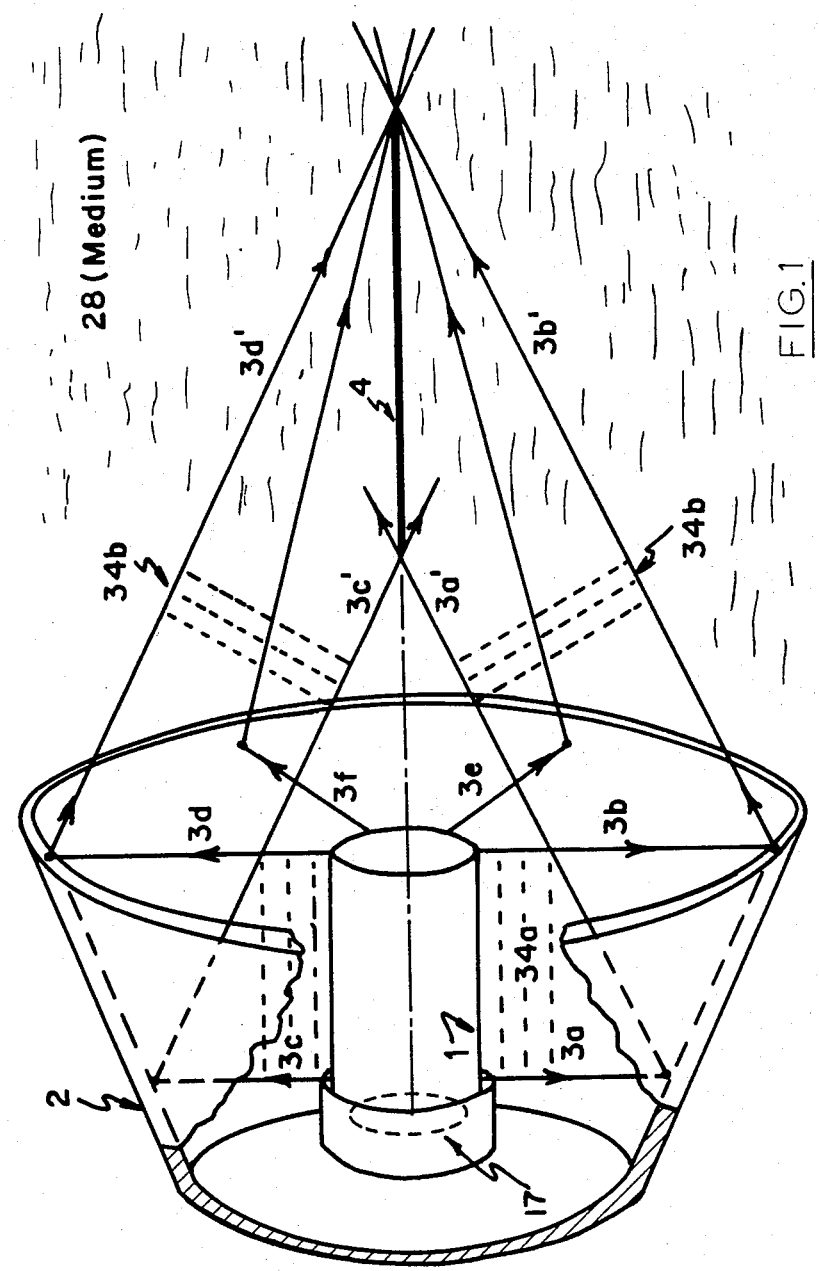
FIG. 1 is a diagrammatic, partially broken away perspective view of a first embodiment of transducer assembly in accordance with the invention, illustrating its focusing action.

Referring to FIG. 1, a piezoelectric ceramic transducer element is fabricated in the shape of a hollow cylinder. Conductive electrodes are painted, baked or evaporated onto the inside and outside surfaces of the cylinder. When an alternating pulsed or continuous wave electrical potential is connected across the electrodes, expanding cylindrical acoustic waves are generated in a surrounding medium 28, typically water. The lines 3a to 3d inclusive indicate typical rays that describe the direction of an ultrasound beam generated by the transducer element. At a range of distances from the axis of the system, the ultrasound beam encounters a concave reflector 2, typically of aluminum or stainless steel, and in the shape of a frustum of a cone. The axis of the reflector is accurately aligned with that of the cylinder. Perfect reflection occurs according to Snell's law, resulting in new rays, 3a' to 3d' inclusive. The conical surface of the reflector thus transforms the cylindrically expanding waves 34a into converging conical waves 34b, which form a sharp focus on a line 4. This focus line 4 is projected in front of the cylindrical transducer and cone assembly; therefore, a sharp focus can be achieved inside a body located so that the focus falls within it. The medium 28 is preferably selected to avoid substantial refraction of the waves at the surface of the body: water provides a suitable match when the body is that of a human patient, or is made of a substance with a density comparable to that of water. It should be noted that the focus on the line 4 differs from a conventional line focus in that the path length of the rays 3a, 3a' and 3c, 3c' is shorter than that of the rays 3b, 3b' and 3d, 3d'. Thus the energy of a wave 34a generated at the outer cylindrical surface of the cylinder 1 will not all arrive at the same instant at the focus line 4. Instead, the corresponding wave 34b will reach the inner end of the line 4 first and then travel to the outer end such that successive waves will scan the line 4.

Except for certain edge effects, waves travelling in directions other than those shown will cancel through destructive interference. Thus sound passing between the transducer surface and the focus line may be represented by rays extending perpendicularly from successive annular increments of the transducer surface, reflected from the surface 2, and converging via paths of successively incremented length at successive focuses along the line 4.

It will be appreciated that the transducer described above can operate in a manner reciprocal to that described so that the transducer element will effectively "see" only incoming acoustic energy from locations on the focus line 4. Thus appropriately directed reflections from a body scanned by a wave front moving along the line 4 will be received by the transducer element over a time period which, because of differences in the reflection path length, will be increased over that in which the wave scans the line 4.

At frequencies of interest in ultrasonic imaging systems and ultrasonic hyperthermy, typically 0.2 to 5 MHz, a piezoelectric ceramic transducer of the cylidrical form described is capable of operating at high efficiencies when coupled into an aqueous medium, typically as high as 80%. Whilst this makes practicable use of the same transducer element for both transmission and reception of ultrasound, this form of operation has the disadvantage that effects due to sidelobes in the radiation pattern are aggravated, thus degrading the quality of the image. For this reason, the transducer is utilized for one only of reception and transmission, the other function being performed by a separate transducer 17 aimed along the axis of the assembly.

Figure 2:
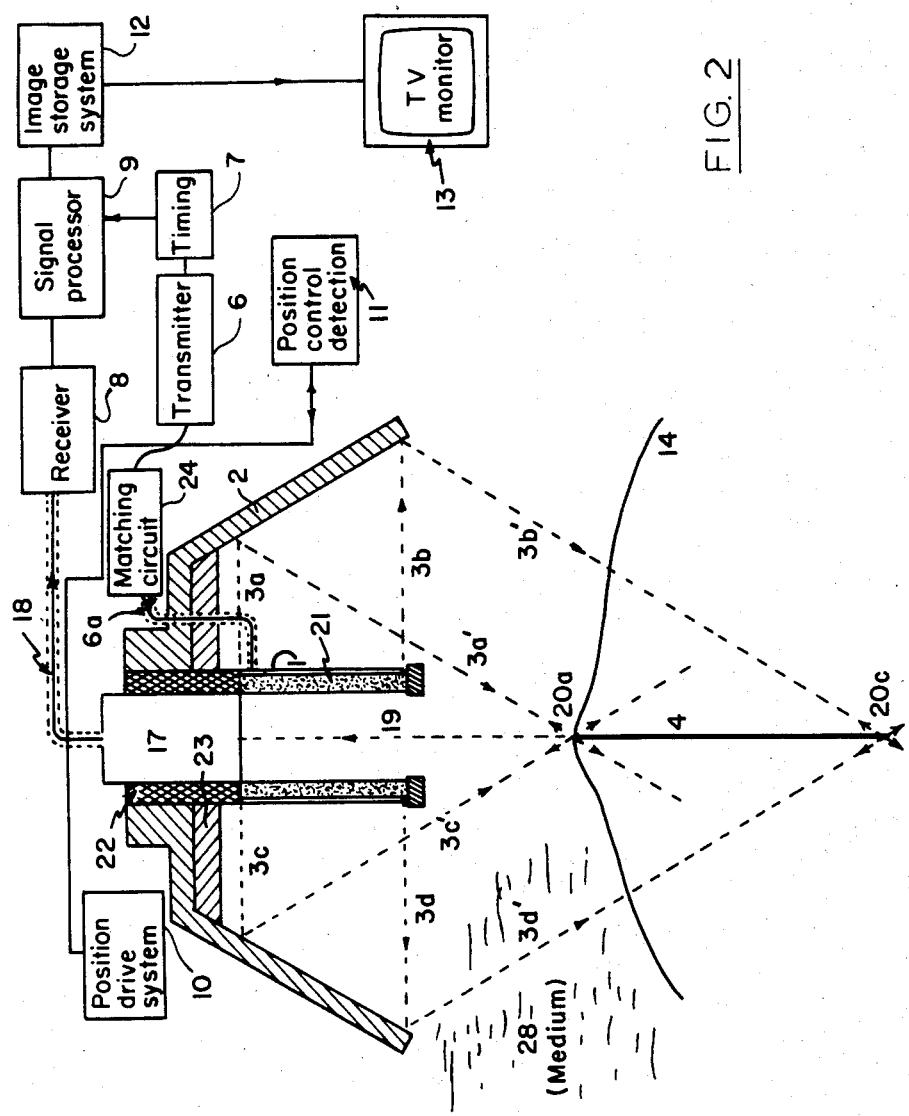
FIG. 2 is a diagrammatic sectional and schematic view illustrating the transducer assembly of FIG. 1 incorporated into an ultrasonic imaging system.

FIG. 2 illustrates an arrangement using the transducer assembly of FIG. 1 which could be used for ultrasonic tomographic imaging of the breast or the abdominal cavity of a human subject. The cylindrical transducer element 1 consists of a high-sensitivity piezoelectric ceramic such as is designated PZT5A or PZT5H. The cylinder may be backed with material 21 such as foam to provide an air space behind the element. Efficiency may be further increased by applying a quarter wavelength thickness of material to the outer surface of the element to improve matching to the medium, thus improving efficiency and bandwidth. A high voltage pulsed radio frequency generator 6, typically providing 30 to 300 volts peak to peak at 2 to 5 MHz, excites the transducer through a matching circuit 24 and a shielded cable 3a, and generates short bursts of ultrasound waves, typically about 1 μsec in length. The waves expand radially as described above with reference to FIG. 1. A timing circuit 7 triggers the transmitter 6 at a repetition frequency of about 1 KHz. The waves are concentrated onto the focus line 4 by the reflecting cone; when scattering structures, such as at 20a and 20c are encountered in a body 14 containing the line 4, the waves are scattered in many directions, including along the line 4, and these last reflections can be detected by a transducer element 17 before the next pulse is generated. The transducer 17 is coaxially aligned with but axially spaced from the focus line 4. Because of the different form of the receiving transducer 17 such a hybrid system displays a marked reduction of sidelobes when operated in pulse-echo mode in an imaging system.

The waves received by the transducer 17 are applied via a cable 18 to a sensitive amplifier in a receiver 8, corrected for tissue attenuation by a signal processor 9, and fed into an image storage system 12 which memorizes the intensity and depth of the scattered waves in the body. A drive system 10 drives the transducer assembly 17 through the water bath 28 on a suitable support assembly in a linear motion (typically 0.5 to 5 seconds per scan). A position control and detection system 11 receives signals from system 10 and coordinates with the storage system 12 to generate tomographic images of the body which are observed on the screen of a monitor 13. The generation of the tomographic image is in accordance with well known techniques which form no part of the invention. It should however be noted that one dimension of the scan is provided automatically by the transducer system.

Because of the focusing properties of the system formed by the cylinder 1 and frustoconical reflector 2, high resolution is achieved at all depths along the focus line 4. The length of the focus line can be increased by reducing the cone angle 15 or increasing the length of the cylindrical transducer. The lateral resolution is related to the transducer frequency (the higher the frequency, the smaller the beam-width), and the cone angle (the larger the value of the cone angle, the smaller the line-focus beam-width). There is, therefore, a compromise between the line-focus length, the cylindrical transducer length, and the cone angle: practically, values of the cone angle $\theta$ from 70° to 55° are preferred. This results in the rays converging on the line 4 at an angle of 50° to 20° to the axis. This last angle should be at least 20° in all cases. It will be appreciated that the cone 2 forms an acoustic reflector system which is associated with the transducer element 1 provides a simulated conical transducer such that the active surface of the element 1 is perceived from the line focus 4 as a conical surface of much larger area and aperture, providing a virtual image of a conical transducer located behind the cone 2 and of greater size and angle than the latter.

Although the dimensions of the unit are not critical, and may be varied to suit the application, a reflector diameter of 15 cm is typical. It should be understood that the apparatus can also be operated with the connections of the cables 3a and 18 interchanged, so that the transducer 17 acts as transmitter.

Figure 3:
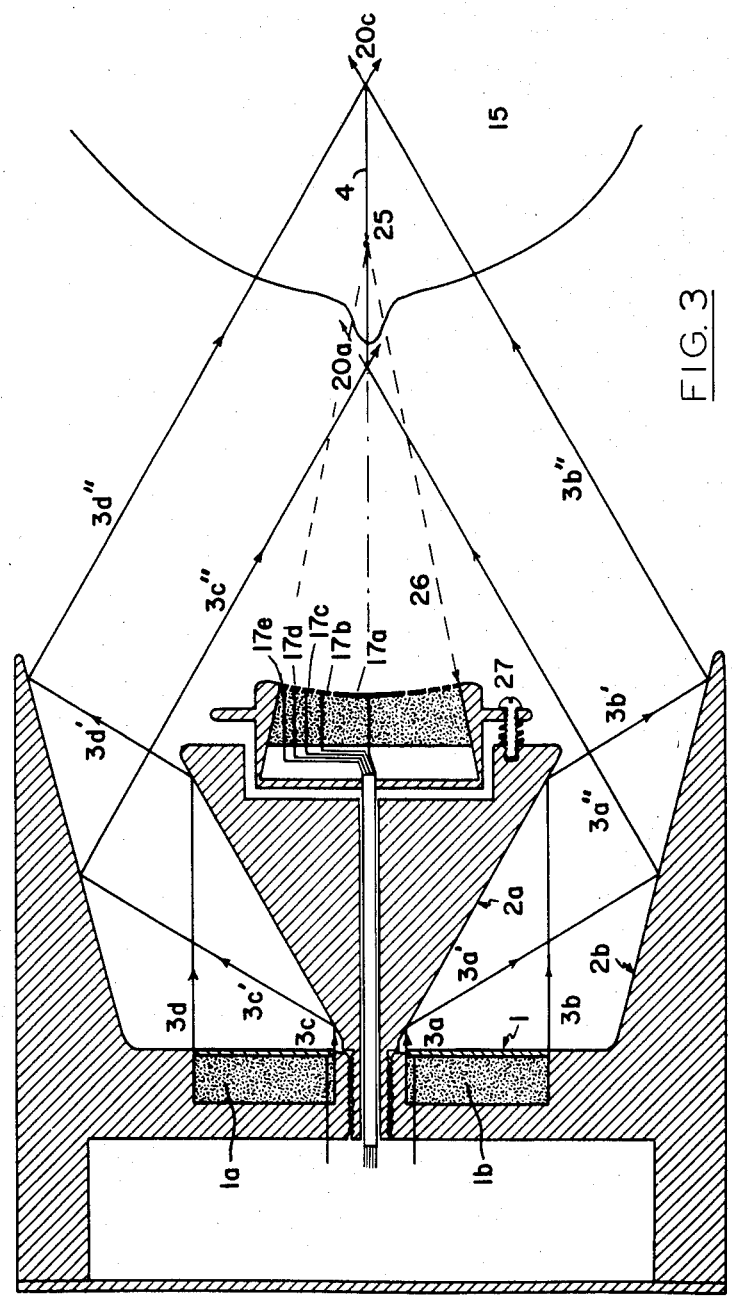
FIG. 3 is a diagrammatic sectional and schematic view illustrating a different embodiment of transducer assembly.

The embodiment of FIG. 3 uses two frustoconical reflecting surfaces to generate the focus line and has the advantage that a conventional readily available and efficient ceramic piezoelectric disc can be used as transducer element 1. This element can be used as either transmitter or receiver in a similar manner to that described with reference to FIG. 2; for purposes of description it is assumed to be the transmitter. A second transducer 17, coaxial with the system axis, receives the scattered waves. The transducer element 1, in this is energized so as to radiate short bursts of ultrasound waves from its free plane annular active surface. These waves are reflected by an acoustic reflector assembly of two frustoconical reflectors. A first convex reflecting surface 2a facing the transducer element 1 transforms the planar waves, limiting rays defining which are shown at 3a, 3b, 3c and 3d, into expanding conical waves, with limiting rays 3a', 3b', 3c' and 3d'. A second reflecting surface 2b facing away from the element 1 produces strongly converging waves, with limiting rays 3a'', 3b'', 3c'' and 3d'', that form a focus line 4 on the axis of the system. An advantage of this geometry is that the sound intensity increases along the focus line 4 extending from 20a to 20c, since successive annular increments of the free transducer surface responsible for the rays converging at successive focuses along the line 4 are of successively increasing circumference and hence area. This partially compensates for losses due to absorption by an object 15 being imaged.

Ultrasound scattered back in near axial directions is received by the coaxial directional transducer 17 mounted on a base of a cone defining the surface 2a. This transducer could be of unitary construction, possibly with a concave free surface to provide it with a compromise focus 25 between the points 20a and 20c and rather nearer the former. Better sidelobe rejection is obtained by using an element in the form of a larger aperture, annular array as shown. This consists of a focused transducer array with a centre portion 17a, and a series of annular ring portions 17b to 17e disposed to define a concave surface of radius of curvature 26. Each portion is of equal area. With such an arrangement, the focus can be scanned electronically in known manner along the line-focus, 20a and 20c, as for example described in an article by M. Arditi, F. S. Foster and J. W. Hunt in Ultrasonic Imaging, Volume 3, pages 37–61 (1981) and M. Arditi, W. B. Taylor, F. S. Foster and J. W. Hunt "An Annular Array System for High Resolution Breast Echography" Ultrasonic Imaging, Vol. 4, 1–31 (1982). Thus waves from point 20a will arrive at portion 17a earlier than at portion 17e. Variable delay lines or equivalent electronic devices are used so that electric signals from portions 17a to 17e are synchronized and are summed together. Similarly, waves from point 20c will arrive at portion 17a later than at portion 17e. Again, similar means are used to correct the time discrepancies. Good resolution can therefore be achieved over the length of the focus line 4 from 20a to 20c. It should be noted that according to reciprocity principles, the spherically shaped transducer, 17a–17e, could just as well be used as the transmitter, and transducer 1 could be the receiver. However, in order to permit signals from the different elements 17a–17e to be differentiated, separate ultrasound pulses must then be focused electronically to form the several focus zones, and must be added together to form a complete scan on line 4. This approach requires multiple excitation pulses, which slows the scanning rate, by a factor of five in the example shown.

A feature of the various embodiments described above is that the transducer 1 or 17 which acts as receiver may in each case be split into a number of pie-shaped segments such as 1a, 1b in FIG. 3. By electronically processing the signals from these segments separately, sidelobe or speckle reduction can be achieved. Sidelobe reduction is accomplished by forming an image in the normal manner and subtracting from it an image containing only sidelobe information. This latter image can be generated by a sidelobe and speckle reduction means incorporated in the signal processor 9 which inverts the signals to or from alternate segments and then sums these signals with uninverted signals from the remaining segments. Speckle reduction is achieved by using the signals from the segments to form images and averaging these images. Whilst images produced in this manner have smoother texture, there is some loss of resolution.

Both sidelobe and speckle reduction can be achieved by multiplying the radio frequency signals from different segments together in the signal processor 9 and using this signal to produce the image.

Although the systems described are intended solely for the purposes of ultrasonic imaging, it should be understood that the invention also finds utility in providing a "view finder" function in hyperthermy systems using a transducer assembly of similar configuration.

It should be understood that the transducer elements need not necessarily be made of piezeoelectric ceramic, and any other element capable of suitable performance may be employed. In the case of apparatus operated at high power levels, quartz crystal elements may be preferred because of their lower temperature sensitivity.

We claim:

1. A transducer assembly for transmitting and receiving ultrasound in an ultrasound imaging system, comprising separate transmitting and receiving transducers, one transducer having a line focus on the axis of a simulated conical active surface and the other transducer being aimed along that axis, characterized in that the simulated conical active surface is a virtual image, formed by an acoustic reflector system, of the active surface of a much smaller transducer element, such that rays from the reflector system converge on the line focus at an angle of at least 20° to the axis.

2. An ultrasonic imaging device, comprising a transducer assembly for transmitting ultrasound pulses into a portion of a structure to be imaged and receiving ultrasound scattered by said structure portion and generating signals in response thereto, means to energize said transducer assembly to transmit said pulses, scanning means for progressively relating said transducer assembly to successive portions of said structure according to a scanning pattern, and receiver and signal processing means for assembling an image from said generated signals, the transducer assembly comprising separate transmitting and receiving transducers, one of said transducers being a simulated conical transducer having a line focus, and the other of said transducers having its axis in parallel alignment with said line focus, the scanning means being operative to move said line focus in relation to a structure to be imaged in accordance with said scanning pattern, wherein the simulated conical transducer comprises a transducer element and an associated acoustic reflector system such that an active surface of the transducer element is perceived at said line focus as a conical transducer having a surface of much larger area than said active surface and having a half angle such that rays converge on said line focus at a predetermined angle of at least 20° to the latter.

3. An ultrasonic imaging device according to claim 2, wherein the active surface of the transducer element is planar and perpendicular to the line focus.

4. An ultrasonic imaging device according to claim 2, wherein the active surface of the transducer element is cylindrical and coaxial with the line focus.

5. An ultrasonic imaging device according to claim 3, wherein the acoustic reflector system comprises a first reflector in the path of plane waves from said planar surface, said first reflector being configured as at least a portion of the external surface of a conical figure of revolution generated about the line of said line focus, and a second reflector in the path of rays from said first reflector to said line focus, said second reflector comprising at least a portion of a figure of revolution generated about said line, said second reflecting surface forming a virtual image of the simulated conical transducer.

6. An ultrasonic imaging device according to claim 5, wherein the transducer element is a disc of piezoelectric material.

7. An ultrasonic imaging device according to claim 2, wherein the rays converge on the the focus line at an angle of between 20° and 50° to its axis.

8. An ultrasonic imaging device according to claim 2, wherein the second transducer is an electronically focused transducer comprising a series of concentric elements.

9. An ultrasonic imaging device according to claim 2, wherein one of the transducers is divided into a plurality of like segments, and means are provided for the selective combination of signals from different segments.

10. An ultrasonic imaging device according to claim 9, wherein the processing means include means to invert the signals from alternate segments, means to sum the inverted signals with the signals from the remaining segments to provide a signal containing only sidelobe information, and means to subtract the sidelobe information signal from the sum of the signals of all the segments.

11. An ultrasonic imaging device according to claim 9, wherein the processing means includes means to form an image from the signal from each segment, and means to average said images.

12. An ultrasonic imaging device according to claim 9, wherein the processing means includes means to multiply the radio frequency signals from each segment together and to use the resultant signal to form the image.

* * * * *